(12) United States Patent
Kim et al.

(10) Patent No.: US 10,912,574 B2
(45) Date of Patent: Feb. 9, 2021

(54) COUPLER ASSEMBLY FOR TIBIAL CUTTING GUIDE

(71) Applicant: CORENTEC CO., LTD., Chungcheongnam-do (KR)

(72) Inventors: Seok-Joo Kim, Gyeonggi-do (KR); Oui-Sik Yoo, Seoul (KR); Chan-Eol Kim, Seoul (KR); Seung-Hun Oh, Seoul (KR)

(73) Assignee: Corentec Co., Ltd., Chungcheongnam-do (KR)

( * ) Notice: Subject to any disclaimer, the term of this patent is extended or adjusted under 35 U.S.C. 154(b) by 509 days.

(21) Appl. No.: 15/576,209

(22) PCT Filed: Mar. 28, 2017

(86) PCT No.: PCT/KR2017/003372
§ 371 (c)(1),
(2) Date: Nov. 21, 2017

(87) PCT Pub. No.: WO2017/171378
PCT Pub. Date: Oct. 5, 2017

(65) Prior Publication Data
US 2018/0344334 A1    Dec. 6, 2018

(30) Foreign Application Priority Data

Mar. 29, 2016 (KR) .................. 10-2016-0037971

(51) Int. Cl.
*A61B 17/17* (2006.01)
*A61B 17/15* (2006.01)
*A61B 17/00* (2006.01)

(52) U.S. Cl.
CPC ........ *A61B 17/1764* (2013.01); *A61B 17/157* (2013.01); *A61B 2017/00477* (2013.01)

(58) Field of Classification Search
CPC .............. A61B 17/157; A61B 17/1682; A61B 17/1764
See application file for complete search history.

(56) References Cited

U.S. PATENT DOCUMENTS 5,275,603 A * 1/1994 Ferrante ............... A61B 17/157
606/86 R
5,628,749 A * 5/1997 Vendrely .............. A61B 17/157
606/80

(Continued)

FOREIGN PATENT DOCUMENTS

JP    2004-202239 A    7/2007
JP    2013-240695 A    12/2013

OTHER PUBLICATIONS

International Search Report dated Jul. 21, 2017 issued in PCT Application No. PCT/KR2017/003372, filed Mar. 28, 2017.
(Continued)

*Primary Examiner* — Anu Ramana
(74) *Attorney, Agent, or Firm* — Workman Nydegger

(57) ABSTRACT

The present invention relates to a coupler assembly for a tibial cutting guide, the assembly including an aligning coupler having a first side coupled to an aligning member by sliding and a second side slid in an adaptor groove of the tibial cutting guide, and a handle slidably coupled to the aligning coupler. More particularly, the present invention relates to a coupler assembly for a tibial cutting guide, the assembly enabling an aligner and a cutting guide to be easily coupled and decoupled through an adaptor without specific operation because when the handle is slid to the cutting guide, the handle is fixed to the cutting guide, and the cutting guide and the adaptor are locked, and when the handle is slid in the opposite direction from the cutting guide, the handle is separated from the cutting guide, and the cutting guide and the adaptor are unlocked.

15 Claims, 15 Drawing Sheets

(56) References Cited

U.S. PATENT DOCUMENTS

| | | | | |
|---|---|---|---|---|
| 5,681,316 | A * | 10/1997 | DeOrio | A61B 17/157 |
| | | | | 606/87 |
| 7,850,698 | B2 * | 12/2010 | Straszheim-Morley | ................. |
| | | | | A61B 17/1764 |
| | | | | 606/102 |
| 7,927,336 | B2 * | 4/2011 | Rasmussen | A61B 17/025 |
| | | | | 606/88 |
| 8,277,450 | B2 * | 10/2012 | Dees, Jr. | A61B 17/154 |
| | | | | 279/42 |
| 8,277,455 | B2 * | 10/2012 | Couture | A61B 17/155 |
| | | | | 606/88 |
| 8,333,772 | B2 * | 12/2012 | Fox | A61B 17/1764 |
| | | | | 606/88 |
| 8,672,946 | B2 * | 3/2014 | Fox | A61B 17/157 |
| | | | | 606/88 |
| 8,828,013 | B2 * | 9/2014 | Fisher | A61B 17/157 |
| | | | | 606/88 |
| 8,834,473 | B2 * | 9/2014 | Dees, Jr. | A61B 17/155 |
| | | | | 606/86 R |
| 2006/0189998 | A1 | 8/2006 | Rasmussen | |
| 2010/0305575 | A1 | 12/2010 | Wilkinson et al. | |

OTHER PUBLICATIONS

Written Opinion dated Jul. 21, 2017, 2017 issued in PCT Application No. PCT/KR2017/003372, filed Mar. 28, 2017.
English translation of Written Opinion dated Jul. 21, 2017, issued in PCT Application No. PCT/KR2017/003372, filed Mar. 28, 2017.

* cited by examiner

COUPLER ASSEMBLY FOR TIBIAL CUTTING GUIDE

TECHNICAL FIELD

The present invention relates to a coupler assembly for a tibial cutting guide, the assembly including an aligning coupler having a first side coupled to an aligning member by sliding and a second side slid in an adaptor groove of the tibial cutting guide, and a handle slidably coupled to the aligning coupler. More particularly, the present invention relates to a coupler assembly for a tibial cutting guide, the assembly enabling an aligner and a cutting guide to be easily coupled and decoupled through an adaptor without specific operation because when the handle is slid to the cutting guide, the handle is fixed to the cutting guide, and the cutting guide and the adaptor are locked, and when the handle is slid in the opposite direction from the cutting guide, the handle is separated from the cutting guide, and the cutting guide and the adaptor are unlocked.

BACKGROUND ART

When a knee joint loses its function due to arthritis or a wound, total joint replacement is operated to restore the normal function of the knee joint by replacing the damaged joint with an implant.

FIGS. 1 to 3 are reference views for illustrating total joint replacement for a knee joint and FIG. 4 is a reference view for illustrating a coupler assembly for a tibial cutting guide of the related art.

Total joint replacement is described in detail with reference to FIGS. 1 to 3. A femoral component 700 is coupled to a femur F, a tibial component 800 is coupled to a tibia T, and a bearing is disposed between the femoral component 700 and the tibial component 800. As for the tibia T, it is required to form a cut surface at the tibia T and a tibial cutting guide (cutting block) R is used to form the cut surface. The tibial cutting guide R is fixed to the tibia T, a cutting blade is inserted into a slot formed in the cutting guide R, and then a cut surface is formed. An aligner is fixed to the tibia T to accurately form a cut surface on the tibia T. The aligner is generally fixed in parallel with the tibia T to be aligned with a mechanical axis and then the aligner and the tibial cutting guide R are combined such that the cutting guide R can be accurately fixed to the tibia T.

However, referring to FIG. 4 to examine the method of combining the tibial cutting guide R and the aligner A in the related art, generally, an aligning member A of the aligner is inserted into a slot H1 of the tibial cutting guide R. Thereafter, a fastener such as a screw S is inserted into a fastener groove H2 of the cutting guide R, thereby fixing the aligning member A and the tibial cutting guide R. Accordingly, the screw S is turned to press the aligning member A when the aligner and the tibial cutting guide are combined, and after the cutting guide R is accurately fixed to the tibia T, the screw S is turned in the opposite direction and then the aligner is separated from the tibial cutting guide R. Accordingly, it is required to operate a specific fastener to combine and separate the parts, so it is relatively troublesome to use the assembly, which causes inconvenience. Further, since a separate operation is required, the surgical operation time is relatively increased, and accordingly, the possibility of excessive bleeding of a patient or aftereffects is inevitably increased.

Korean Patent No. 10-0431911 relates to a tibial resection instrument. In detail, the instrument is equipment for preparing a proximal tibia of a patient and includes a body 22, an insertion rod 21 for tracing a tube in marrow, a cutting guide 20 for guiding a cutting blade when cutting a tibia of a patient, and a means for setting the cutting depth in the tibia.

According to the instrument, separate fasteners such as set screws 32 and 57 are used to combine and separate an aligning sleeve 18, a cutting guide 20, a vertical post 36, a beam 51 etc., so the configuration is complicated and the combination method is also relatively complicated. Accordingly, the possibility of delay of a surgical operation, excessive bleeding, and aftereffects is inevitably relatively high.

Accordingly, there is a need for a combination method that can relatively reduce operation time and minimize the possibility of excessive bleeding of a patient and aftereffects by which a tibial cutting guide and an aligner can be simply combined and separated without operating specific parts.

DISCLOSURE

Technical Problem

The present invention has been made in an effort to solve the problems.

An object of the present invention is to provide a coupler assembly for a tibial cutting guide, the assembly being able to reduce a surgical operation time and minimize bleeding of a patient and aftereffects, because the cutting guide and a guide adaptor can be coupled without a specific operation through the guide adaptor that is movably coupled to an aligning member and can easily detachably couple the tibial cutting guide to the aligning member.

Another object of the present invention is to provide a coupler assembly for a tibial cutting guide, the assembly c an adaptor and the cutting guide to be easily coupled and decoupled, because when a handle is slid to the cutting guide, the handle is fixed to the cutting guide, and the cutting guide and the adaptor are locked, and when the handle is slid in the opposite direction from the cutting guide, the handle is separated from the cutting guide, so the cutting guide and the adaptor are unlocked.

Another object of the present invention is to provide a coupler assembly for a tibial cutting guide, the assembly enabling an aligning member and the cutting guide to be easily coupled and decoupled, because when a handle is slid to the cutting guide, a pin is inserted into a side of the cutting guide, so the adaptor and the cutting guide are locked and cannot be vertically separated, and when the handle is slid in the opposite direction to the cutting guide, the pin is pulled out, so the adaptor and the cutting guide are unlocked and can be vertically separated.

Another object of the present invention is to provide a coupler assembly for a tibial cutting guide, the assembly enabling an aligning member and the cutting guide to be easily coupled and decoupled without specific operation, because when a handle is slid to the cutting guide, pins inserted in first pin holes of grips are inserted into pin insertion holes of the cutting guide for locking, and when the handle is slid away from the cutting guide, the pins inserted in the pin insertion holes are pulled out.

Another object of the present invention is to provide a coupler assembly for a tibial cutting guide, the assembly enabling easy coupling of a handle and an aligning coupler and preventing vertical separation of the handle and the aligning coupler because the handle and the aligning coupler can be coupled by sliding through a slide groove formed on a side of the handle and sliding flanges formed on sides of the aligning coupler.

Another object of the present invention is to provide a coupler assembly for a tibial cutting guide, the assembly being able to prevent an adaptor from separating forward and backward from the cutting guide because an insertion rod is inserted in an adaptor groove of the tibial cutting guide.

Another object of the present invention is to provide a coupler assembly for a tibial cutting guide, the assembly enabling an aligning member and an adaptor to be firmly coupled by restricting slide of member holders with respect to the aligning member because when the handle is coupled to an aligning coupler by sliding, grips press the member holders disposed inside the grips.

Another object of the present invention is to provide a coupler assembly for a tibial cutting guide, the assembly preventing an aligning coupler coupled to a handle by sliding from separating forward and backward through a second pin hole formed at a side of the top of a connecting portion of the handle and a third pin hole formed at a side on the top of an insertion rod of the aligning coupler.

Another object of the present invention is to provide a coupler assembly for a tibial cutting guide, the assembly being able to lock and unlock the cutting guide and an adaptor by enabling a handle coupled to an aligning coupler to slide a predetermined distance forward and backward by forming an oblong third pin hole.

Another object of the present invention is to provide a coupler assembly for a tibial cutting guide, the assembly being able to provide safety in use through a ball hole formed at a predetermined depth on the top of an insertion rod to receive a ball plunger therein and a ball receiving hole formed at a predetermined depth at a side of the top of a slide groove of a connecting portion to lock and unlock a guide adaptor through a ball of the ball plunger received in the ball hole.

Another object of the present invention is to provide a coupler assembly for a tibial cutting guide, the assembly being able to further provide safety in use because a first ball receiving hole and a second ball receiving hole of a connecting portion guide the cutting guide and an adaptor when they are locked and unlocked.

Another object of the present invention is to provide a coupler assembly for a tibial cutting guide, the assembly being able to further firmly couple an insertion rod being in contact with the cutting guide to the cutting guide because it has a magnet hole formed at a predetermined depth at a side of the insertion rod to receive a magnet therein.

Another object of the present invention is to provide a coupler assembly for a tibial cutting guide, the assembly being able to easily couple the cutting guide and an adaptor to each other by reducing interference between edges when an aligning coupler is inserted into an adaptor groove because chamfered edges are formed at a predetermined angle at both edges of a distal side of an insertion rod and rounded corners are formed at the corners of the bottom.

Technical Solution

The present invention is achieved by an embodiment having the following configuration to accomplish the objects.

A coupler assembly for a tibial cutting guide according to an embodiment of the present invention includes a guide adaptor for holding the tibial cutting guide on an aligning member, in which the guide adaptor is movably coupled to the aligning member so that the tibial cutting guide can be easily detachably coupled to the aligning member.

According to another embodiment, the guide adaptor may have an aligning coupler slidably coupled to the aligning member and the cutting guide, and a handle slidably coupled to the aligning coupler, and the handle may be detachably coupled to the tibial cutting guide by being slid on the aligning coupler According to another embodiment of the present invention, the direction in which the handle of the coupler assembly for a tibial cutting guide is slid with respect to the aligning coupler may be substantially perpendicular to the direction in which the aligning coupler is slid to the aligning member.

According to another embodiment of the present invention, when the handle of the coupler assembly for a tibial cutting guide is slid to the cutting guide, the handle may be fixed to the cutting guide, so the cutting guide and the adaptor may be locked, and when the handle is slid in an opposite direction from the cutting guide, the handle may be separated from the cutting guide, so the cutting guide and the adaptor may be unlocked.

According to another embodiment of the present invention, the handle of the coupler assembly for a tibial cutting guide may have grips formed in pairs facing each other to form a predetermined space therebetween and sliding on the aligning coupler to be coupled to and decoupled from the cutting guide, and the grips may each have a first pin hole formed at a side of each distal side at a predetermined depth to receive a pin, when the handle is slid to the cutting guide with the first pin holes and pin insertion holes of the cutting guide aligned, the pins in the first pin holes may be inserted into the pin insertion holes, so the handle and the cutting guide may be locked, and when the handle is slid in an opposite direction, the pins may be pulled out of the pin insertion holes, so the handle and the cutting guide may be unlocked.

According to another embodiment of the present invention, the handle of the coupler assembly for a tibial cutting guide may further have a connecting portion integrally formed with the grips and coupled to the aligning coupler by sliding, the connecting portion may have a T-shaped slide groove formed on a bottom with a predetermined length and may enable the handle and the aligning coupler to be coupled by sliding, the aligning coupler may have a pair of member holders facing each other and having a groove having a predetermined shape on an inner side, and a rod integrally formed with the member holders and having a first side coupled to the handle by sliding and a second side slid in an adaptor groove of the cutting guide, and the rod may have T-shaped sliding flanges protruding downward a predetermined length from tops of both sides so that the handle and the aligning coupler can be coupled by sliding.

According to another embodiment of the present invention, when the handle and the aligning coupler of the coupler assembly for a tibial cutting guide are coupled by sliding, the grips may press the member holders positioned inside the grips, so sliding of the member holders with respect to the aligning member may be restricted, whereby the aligning member and the adaptor may be firmly coupled.

According to another embodiment of the present invention, the connecting portion of the coupler assembly for a tibial cutting guide may further have a second pin hole formed vertically through a side to receive a pin, the rod may further have a third pin hole formed at a predetermined depth at a side on a top to receive a pin, and the handle may be prevented from sliding from the aligning coupler by a pin inserted in the second pin hole and the third pin hole.

According to another embodiment of the present invention, the third pin hole of the coupler assembly for a tibial cutting guide may be formed in an oblong shape and enable the handle coupled to the aligning coupler by sliding to slide a predetermined distance forward and backward so that the cutting guide and the adaptor can be coupled and decoupled.

According to another embodiment of the present invention, the rod of the coupler assembly for a tibial cutting guide may further have a ball hole formed at a predetermined depth at another side on the top to receive a ball plunger therein, and the connecting portion may further have a ball receiving hole formed at a predetermined depth on a top of the slide groove and receive a ball of the ball plunger to guide the adaptor when the adaptor is locked and unlocked.

According to another embodiment of the present invention, the ball receiving hole of the coupler assembly for a tibial cutting guide may include a first ball receiving hole formed at a predetermined depth at a side on the top of the slide groove and receives the ball in locking and a second ball receiving hole formed at a predetermined depth at a predetermined distance from the first ball hole and receives the ball in unlocking.

According to another embodiment of the present invention, when the handle and the aligning coupler of the coupler assembly for a tibial cutting guide are coupled by sliding, center points of the first ball receiving hole and the second ball receiving hole may be positioned on an axis of the third pin hole so that the adaptor and the cutting guide can be coupled and decoupled by accurately sliding the handle coupled to the aligning coupler.

According to another embodiment of the present invention, the rod of the coupler assembly for a tibial cutting guide may further have a magnet hole formed at a side of a proximal side to receive a magnet therein, so the cutting guide and the guide adaptor may be firmly coupled by attraction of the magnet.

According to another embodiment of the present invention, the magnet disposed in the magnet hole of the coupler assembly for a tibial cutting guide may be a neodymium magnet.

According to another embodiment of the present invention, the rod of the coupler assembly for a tibial cutting guide may further have chamfered edges formed by cutting edges of both sides of a distal side at a predetermined angle to minimize interference between edges for easy coupling when the aligning coupler is inserted into the adaptor groove.

According to another embodiment of the present invention, the rod of the coupler assembly for a tibial cutting guide may further have rounded corners formed by rounding bottoms of both edges of both sides of the distal side to minimize interference between the edges for easy coupling when the aligning coupler is inserted into the adaptor groove.

Advantageous Effects

The present invention can obtain the following effects from the embodiments, and the configurations and combination and use relationships to be described below.

It is possible to reduce a surgical operation time and minimize bleeding of a patient and aftereffects, because a cutting guide and a guide adaptor can be coupled without specific operation through the guide adaptor that is movably coupled to an aligning member and can easily detachably couple the tibial cutting guide to the aligning member.

It is possible to enable an adaptor and a cutting guide to be easily coupled and decoupled, because when a handle is slid to the cutting guide, the handle is fixed to the cutting guide, and the cutting guide and the adaptor are locked, and when the handle is slid in the opposite direction from the cutting guide, the handle is separated from the cutting guide, so the cutting guide and the adaptor are unlocked.

It is possible to enable an aligning member and a cutting guide to be easily coupled and decoupled, because when a handle is slid to the cutting guide, a pin is inserted into a side of the cutting guide, so the adaptor and the cutting guide are locked and cannot be vertically separated, and when the handle is slid in the opposite direction to the cutting guide, the pin is pulled out, so the adaptor and the cutting guide are unlocked and can be vertically separated.

It is possible to enable an aligning member and a cutting guide to be easily coupled and decoupled without specific operation, because when a handle is slid to the cutting guide, pins inserted in first pin holes of grips are inserted into pin insertion holes of the cutting guide for locking, and when the handle is slid away from the cutting guide, the pins inserted in the pin insertion holes are pulled out.

It is possible to enable easy coupling of a handle and an aligning coupler and prevent vertical separation of the handle and the aligning coupler, because the handle and the aligning coupler can be coupled by sliding through a slide groove formed on a side of the handle and sliding flanges formed on sides of the aligning coupler.

It is possible to prevent an adaptor from separating forward and backward from the cutting guide, because an insertion rod is inserted in an adaptor groove of the tibial cutting guide.

It is possible to enable an aligning member and an adaptor to be firmly coupled, by restricting sliding of member holders with respect to the aligning member because when the handle is coupled to an aligning coupler by sliding, grips press the member holders disposed inside the grips.

It is possible to prevent an aligning coupler coupled to a handle by sliding from separating forward and backward through a second pin hole formed at a side of the top of a connecting portion of the handle and a third pin hole formed at a side on the top of an insertion rod of the aligning coupler.

It is possible to lock and unlock the cutting guide and an adaptor by enabling a handle coupled to an aligning coupler to slide a predetermined distance forward and backward by forming an oblong third pin hole.

It is possible to provide safety in use through a ball hole formed at a predetermined depth on the top of an insertion rod to receive a ball plunger therein and a ball receiving hole formed at a predetermined depth at a side of the top of a slide groove of a connecting portion to lock and unlock a guide adaptor through a ball of the ball plunger received in the ball hole.

It is possible to further provide safety in use because a first ball receiving hole and a second ball receiving hole of a connecting portion guide the cutting guide and an adaptor when they are locked and unlocked.

It is possible to further firmly couple an insertion rod being in contact with the cutting guide to the cutting guide because the assembly has a magnet hole formed at a predetermined depth at a side of the insertion rod to receive a magnet therein.

It is possible to easily couple the cutting guide and an adaptor to each other by reducing interference between edges when an aligning coupler is inserted into an adaptor groove because chamfered edges are formed at a predetermined angle at both edges of a distal side of an insertion rod and rounded corners are formed at the corners of the bottom.

BEST MODE

Figure 1:
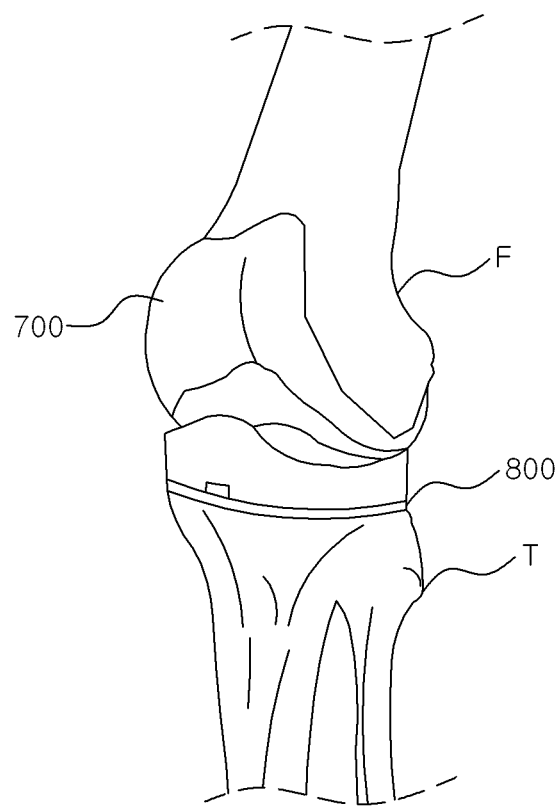
FIGS. 1 to 3 are reference views for illustrating total joint displacement of a knee joint.
Figure 2:
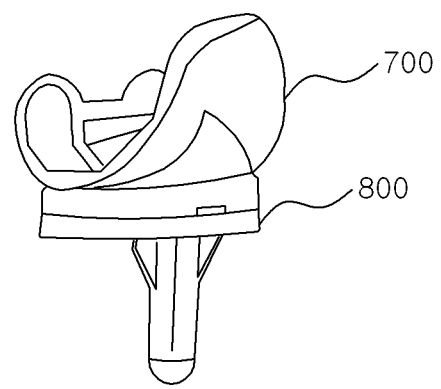
Figure 3:
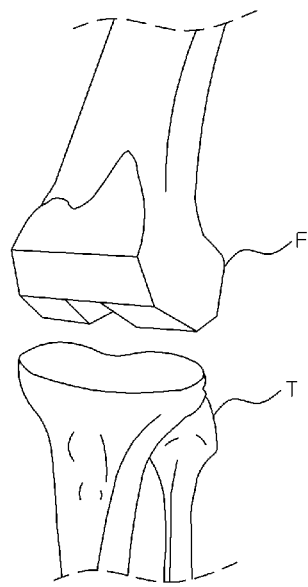
Figure 4:
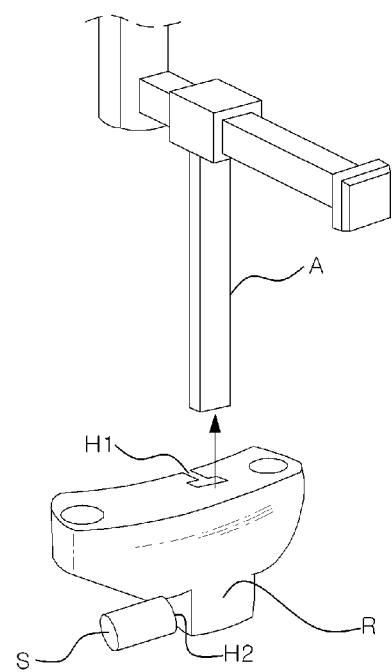
FIG. 4 is a reference view of illustrating a coupler assembly for a tibial cutting guide of the related art.

Hereinafter, a coupler assembly for a tibial cutting guide according to the present invention will be described with reference to the accompanying drawings. It should be noted that the same components are given the same reference numerals in any drawings. Further, well-known functions and configurations that may unnecessarily make the spirit of the present invention unclear are not described in detail. Unless specifically stated, all terms used herein are the same as normal meanings of terms that those skilled in the art understand, but follow the meanings defined herein if they are different from the normal meanings.

Figure 5:
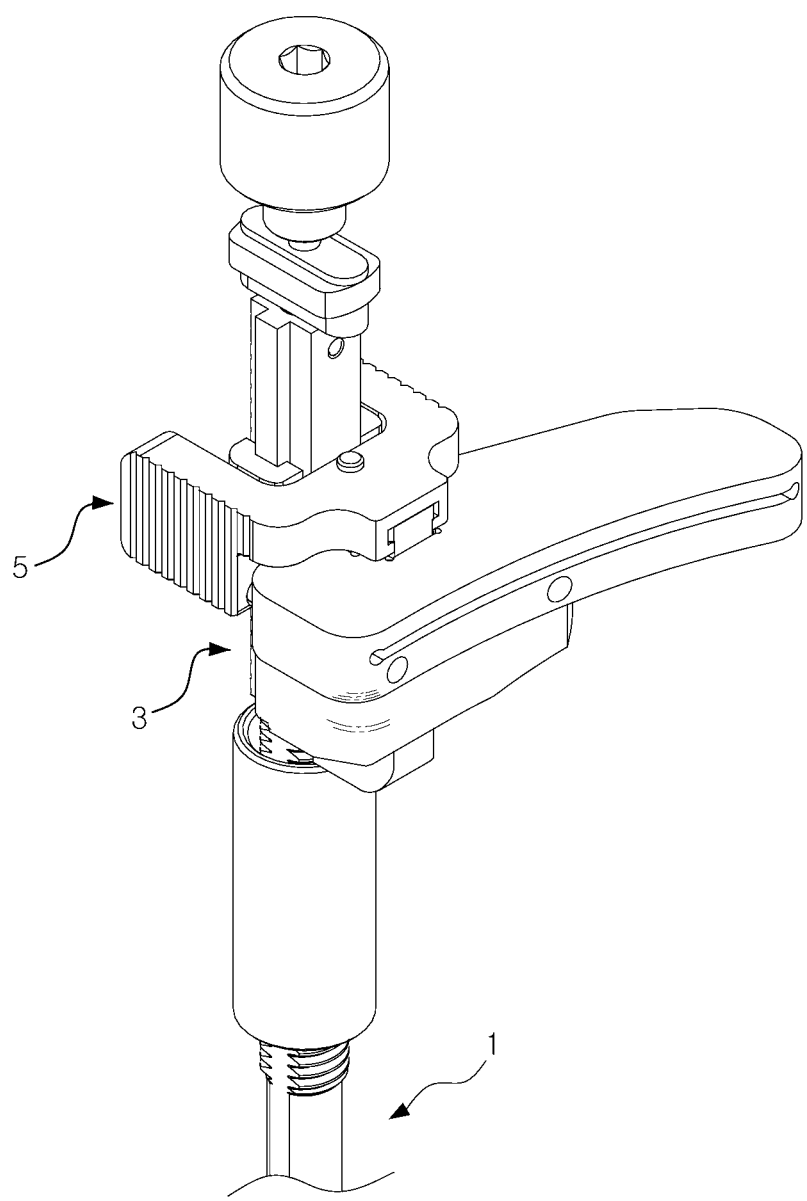
FIG. 5 is a perspective view of a coupler assembly for a tibial cutting guide according to an embodiment of the present invention.
Figure 6:
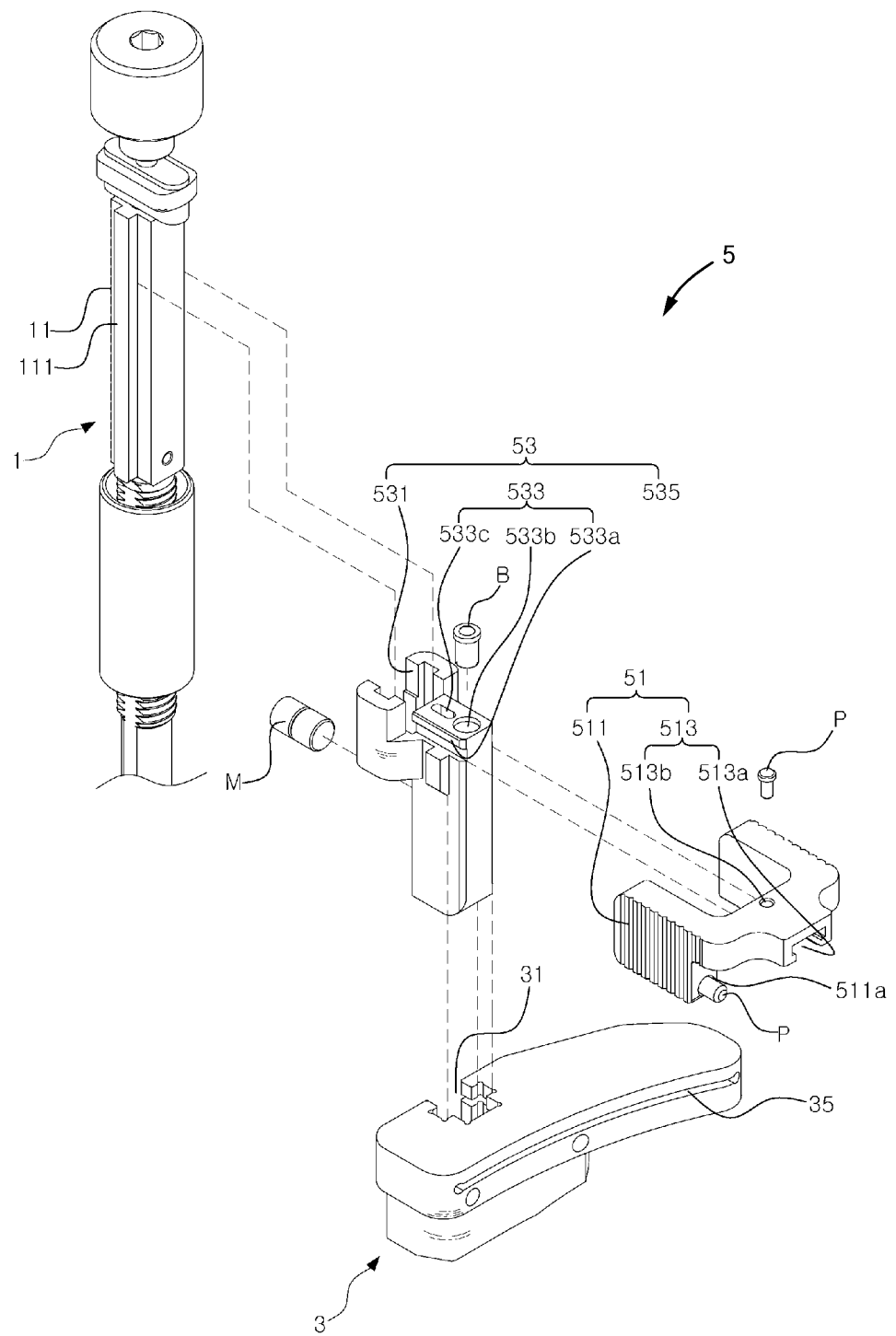
FIG. 6 is an exploded perspective view of the coupler assembly for a tibial cutting guide shown in FIG. 5.
Figure 7:
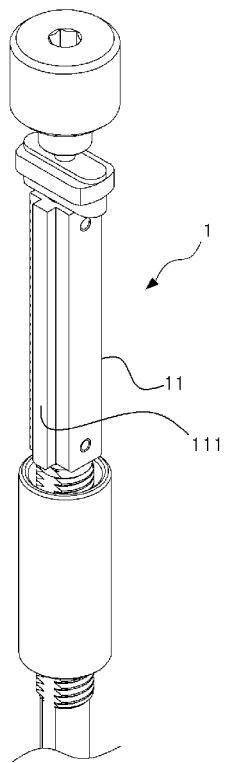
FIG. 7 is a perspective view of the aligner shown in FIG. 5.
Figure 8:
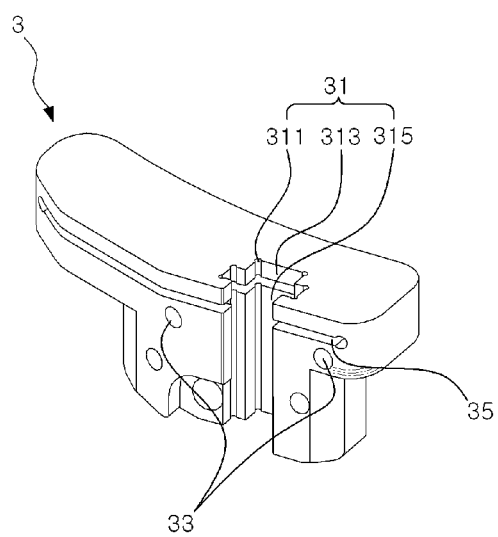
FIG. 8 is a perspective view of the tibial cutting guide shown in FIG. 5.
Figure 9:
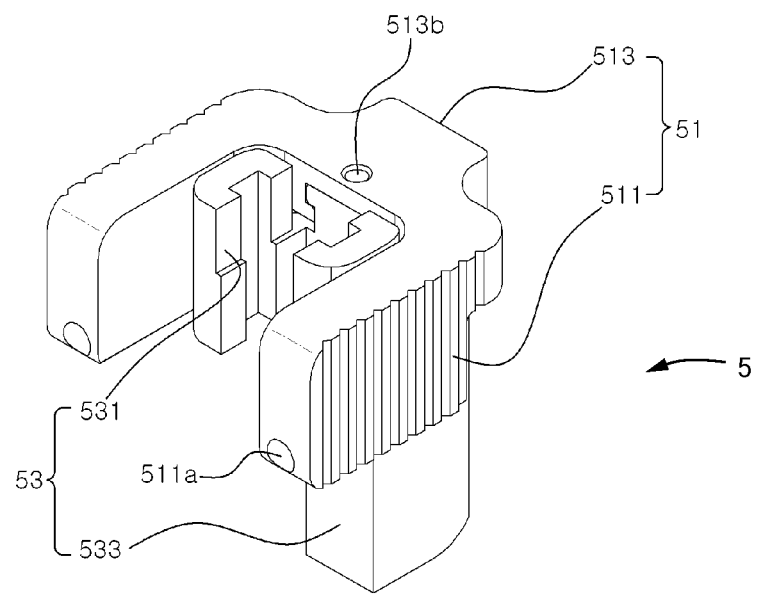
FIG. 9 is a perspective view of the guide adaptor shown in FIG. 5.
Figure 10:
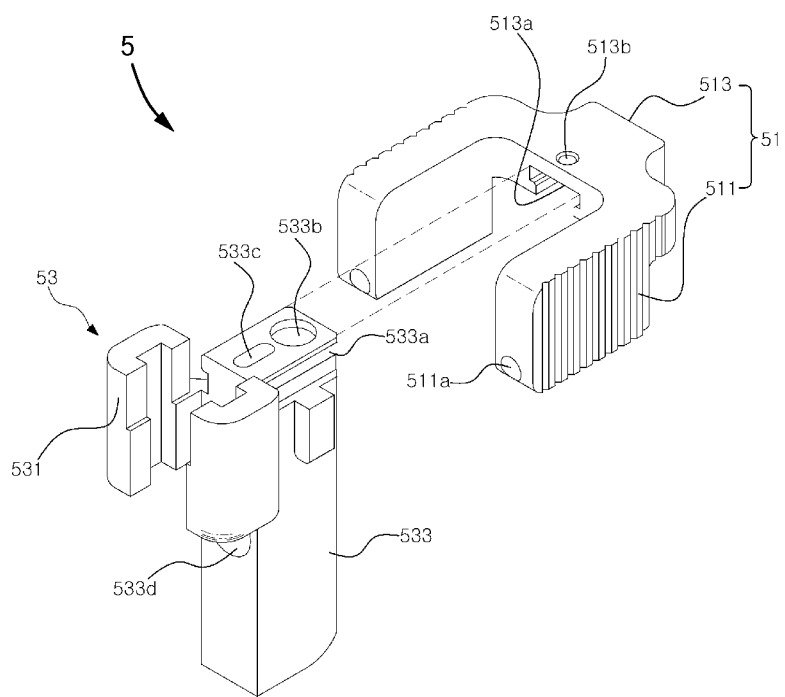
FIG. 10 is an exploded perspective view of the guide adaptor shown in FIG. 9.
Figure 11:
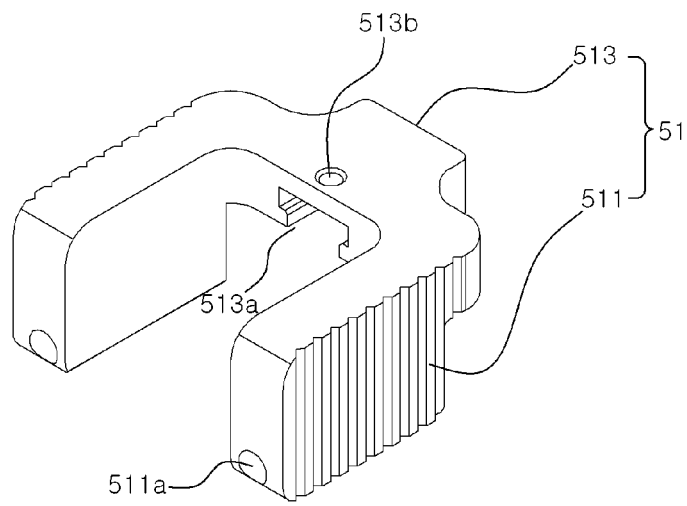
FIG. 11 is a perspective view of the handle shown in FIG. 9.
Figure 12:
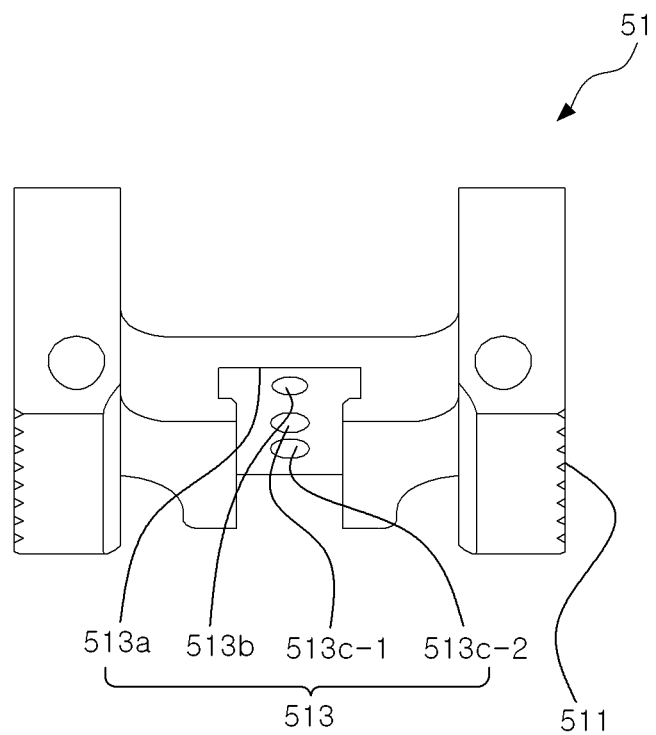
FIG. 12 is a bottom view of the handle shown in FIG. 11.
Figure 13A:
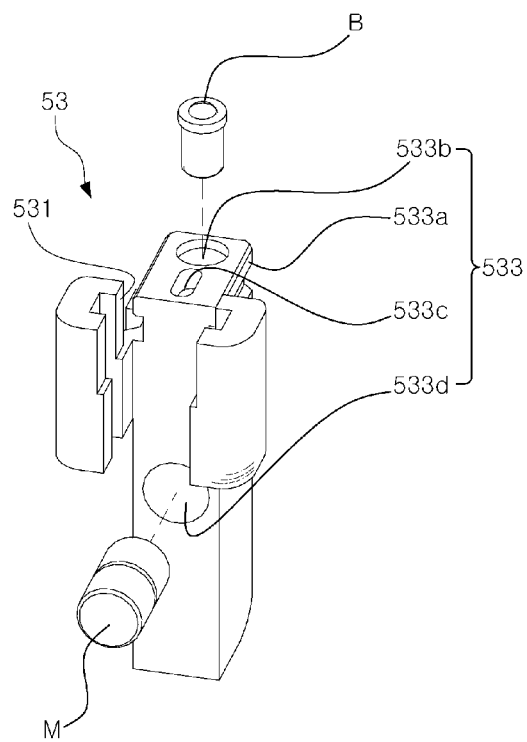
FIGS. 13A, 13B and 14 are perspective views showing the aligning coupler shown in FIG. 9.
Figure 13B:
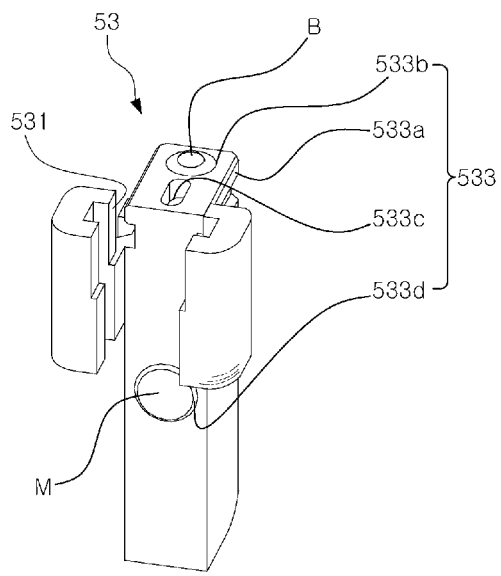
Figure 14:
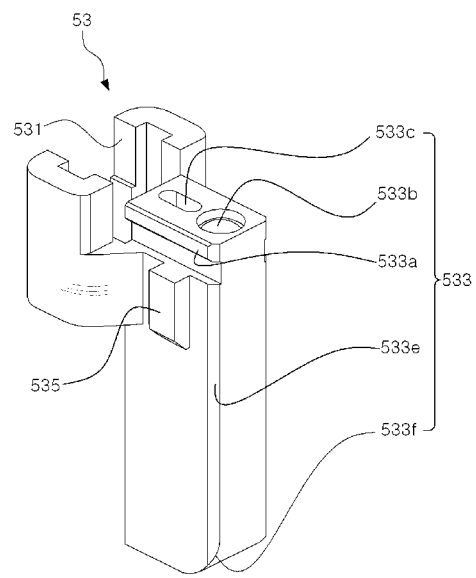

FIG. 5 is a perspective view of a coupler assembly for a tibial cutting guide according to an embodiment of the present invention, FIG. 6 is an exploded perspective view of the coupler assembly for a tibial cutting guide shown in FIG. 5, FIG. 7 is a perspective view of the aligner shown in FIG. 5, FIG. 8 is a perspective view of the tibial cutting guide shown in FIG. 5, FIG. 9 is a perspective view of the guide adaptor shown in FIG. 5, FIG. 10 is an exploded perspective view of the guide adaptor shown in FIG. 9, FIG. 11 is a perspective view of the handle shown in FIG. 9, FIG. 12 is a bottom view of the handle shown in FIG. 11, and FIGS. 13 and 14 are perspective views showing the aligning coupler shown in FIG. 9.

A coupler assembly for a tibial cutting guide according to an embodiment of the present invention is described with reference to FIGS. 5 and 6. The assembly may include an aligner 1 that is generally disposed in parallel with a tibia T of a patient and aligned with a mechanical axis of the tibia T, a tibial cutting guide 3 for forming a cut surface on the tibia T, and a guide adaptor 5 that is movably combined with an aligning member 11 so that the tibial cutting guide 3 is easily coupled to/decoupled from the aligning member 11. According to the coupler assembly for a tibial cutting guide, the aligner 1 and the tibial cutting guide 3 can be easily and quickly coupled and decoupled through the guide adaptor 5, so it is possible to minimize excessive bleeding and after-effects by reducing surgical operation time. To this end, the coupler assembly may include the aligner 1, the tibial cutting guide 3, and the guide adaptor 5. In the following description, the sides of the components that face the tibia T when a side of the cutting guide 3 is attached to the proximal end of the tibia T by combining the components are defined as distal sides and the sides opposite to the distal sides are defined as proximal sides.

Referring to FIGS. 5 to 7, the aligner 1 is generally arranged in parallel with the tibia T to be aligned with a mechanical axis so that the tibia cutting guide 3 can form an accurate cut surface, and to this end, the aligner 1 may include the aligning member 11.

The aligning member 11 vertically extends a predetermined length from a side of the aligner 1 such that the guide adaptor 5 to be described below can be movably coupled to the aligning member 11 by sliding. For example, the aligning member 11 may be inserted in a groove defined by member holders 531, which will be described below, of the guide adaptor 5 to be coupled to the guide adaptor 5 by sliding. To this end, the aligning member 11 may have projective rails 111.

The projective rails 111 extend from an end to the other end of both sides of the aligning member 11 and have predetermined width and height, and they may be formed in a hexahedral shape. Accordingly, for example, the projective rails 111 are inserted in a cross-shaped groove defined by the member holders 531 to be described below, whereby the aligner 1 and the guide adaptor 5 can be combined.

Referring to FIGS. 5, 6, and 8, the tibial cutting guide 3 is used to form a cut surface on the proximal end of the tibia T to seat a tibial component and a flat cutter blade such as a cutting blade is inserted in a slot 35 formed on a side of the tibial cutting guide 3 to form a cut surface on the tibia T. To this end, the tibial cutting guide 3 has an adaptor groove 31, pin insertion holes 33, and the slot 35.

The adaptor groove 31 is vertically formed from a side, for example, the top of the cutting guide 3 and holds a side of the guide adaptor 5 so that the guide adaptor 5 and the tibial cutting guide 3 can be combined by sliding. The adaptor groove 31 may be formed, for example, as a cross-shaped groove, but the shape is not limited. To this end, the adaptor groove 31 may have anti-interference grooves 311, a first groove 313, and a second groove 315.

Referring to FIG. 8, the anti-interference grooves 311 are formed by rounding the corners of the adaptor groove 31 so that cross-shaped projections 535 can be easily inserted into the adaptor groove 31 by minimizing interference among their corners.

The first groove 313 vertically extends downward a predetermined length on the inner side from the top of the adaptor groove 31, in detail, extends to the slot 35 formed inside the adaptor groove 31. The first groove 313 may be formed, for example, in a cross shape.

The second groove 315 extends up a predetermined length on the inner side from the bottom of the adaptor groove 31, in detail, extends to the slot 35 formed inside the adaptor groove 31. The second groove 315 may be formed, for example, in a cross shape.

The pin insertion holes 33 are formed at a predetermined depth from a side of the proximal side of the tibial cutting guide 3 and pins P in first pin holes 511a to be described below are inserted into and pulled out of the pin insertion holes 33 so that the tibial cutting guide 3 and the guide adaptor 5 can be separably combined. In detail, when the top of the adaptor groove 31 of the cutting guide 3 is placed on the bottoms of the cross-shaped projections 535 of the guide adaptor 5 and then the cutting guide 3 is slid up, the cross-shaped projections 535 are brought in close contact with the first and second grooves 313 and 315, whereby the cutting guide 3 and the adaptor 5 are combined. Thereafter, when the pin insertion holes 33 and the first pin holes 511a are aligned, the handle 51 to be described below is slid to the cutting guide 3. Accordingly, the pins P protruding out of the first pin holes 511a of the adaptor 5 are inserted into the pin insertion holes 33, so the cutting guide 3 and the adaptor 5 are locked to each other.

The slot 35 is formed from the proximal side to the distal side of the tibial cutting guide 3 to receive a cutting member (not shown) such as a cutting blade for forming a cut surface and has a predetermined shape, but it may have a rectangular shape.

Referring to FIGS. 9 and 10, the guide adaptor 5 holds the tibial cutting guide 3 on the aligning member 11, in detail, is movably coupled to the aligning member 11 so that the cutting guide 3 is easily separably coupled to the aligning member 11. For example, the guide adaptor is fixed to the aligning member 11 on a side, is received in the adaptor groove 31 of the tibial cutting guide 3 at the other side, and is fastened to the cutting guide 3 by the pins P so that the aligner 1 and the tibial cutting guide 3 can be easily combined and separated. To this end, the coupler assembly may include the handle 51 and the aligning coupler 53. As described above, in the related art, the aligner 1 and the cutting guide 3 are coupled by inserting the tibial cutting guide 3 into the groove of the aligner 1 and then tightening fasteners such as screws into the fastener holes formed at a side of the aligner 1, and they are decoupled by loosening the fasteners, so it is relatively troublesome work. In order to solve this problem, according to the present invention, the aligner 1 and the tibial cutting guide 3 are easily coupled and decoupled by the guide adaptor 5 that is an additional component, which will be described in detail below.

Referring to FIGS. 9 to 11, the handle 51 is slidably coupled to the aligning coupler 53 to be detachably coupled to the tibial cutting guide 3. In detail, when the handle 51 is slid to the cutting guide 3, the handle 5 is fixed to the cutting guide 3, whereby the cutting guide 3 and the adaptor 5 are locked (coupled). Further, when the handle 51 is slid in the opposite direction from the cutting guide 3, the handle 51 is decoupled from the cutting guide 3 and unlocked (separated). For example, when the first pin holes 511a and the pin insertion holes 33 are aligned and then the handle 51 is slid to the cutting guide 3, the pins P inserted in a side of the handle 51 are inserted into the pin insertion holes 33, so the handle 51 is locked. Further, when the handle 51 is slid in the opposite direction from the cutting guide 3, the pins P are pulled, so the handle 51 is unlocked. The direction in which the handle 51 is slid with respect to the aligning coupler 53 may be substantially perpendicular to the direction in which the aligning coupler 53 is slid to the aligning member 11. To this end, the handle 51 may have grips 511 and a coupling portion 513.

The grips 511 are formed in pairs facing each other to form a predetermined space therebetween and slidably coupled to the aligning coupler 53 to be detachably coupled to the tibial cutting guide 3. For example, the adaptor 5 may be detachably coupled to the cutting guide 3 by pins. A plurality of grooves is formed with regular intervals on the grips 511 so that a user can easily hold the handle. To this end, the first pin holes 511a may be formed at the grips 511.

The first pin holes 511a may be formed at a side of each of the grips 511, for example, at a side of the distal sides at a predetermined depth to receive pins P. Accordingly, in order to couple the tibial cutting guide 3 and the guide adaptor 5, a side of the aligning coupler 53 is inserted into the adaptor groove 31 of the cutting guide 3 and then the handle is slid to the aligner 3 with the first pin holes 511a aligned with the pin insertion holes 33. Accordingly, the pins P in the first pin holes 511a are moved into the pin insertion holes 33 of the tibial cutting guide 3, so the cutting guide 3 and the adaptor 5 are prevented from vertically separating (locked). Further, for decoupling of the cutting guide 3 and the adaptor 5, the handle 51 is slid in the opposite direction from the tibial cutting guide 3 coupled to the proximal end of the tibia T, so they can be easily separated without specific operation (unlocked). The number of the first pin holes 511a is not limited, but one may be formed at each of the grips 511.

Referring to FIGS. 9 to 12, the connecting portion 513 is integrally formed with both grips 511 to connect the grips 511 to each other, is slidably coupled to the aligning coupler 53 to be described below, and has a side seated on the top of the cutting guide 3. To this end, the connecting portion 513 may have a slide groove 513a, a pin hole 513b, and a ball receiving hole 513c.

The slide groove 513a is formed on a side of the connecting portion 513, in detail, it may be formed with a predetermined length in a T-shape on the bottom so that the handle 51 and the aligning coupler 53 to be described below can be coupled by sliding. Accordingly, it is possible to easily couple the handle 51 and the aligning coupler 53 and it is also possible to prevent vertical separation (drop) of the handle 51 and the aligning coupler 53. Further, the handle 51 can slide a predetermined distance forward and backward after being coupled to the aligning coupler 53, which will be described in detail below.

The second pin hole 513b is formed vertically through a side of the connecting portion 513 so that a pin P for coupling the handle 51 and the aligning coupler 53 is inserted therein. Sliding of the handle 51 and the aligning coupler 53 is suppressed by inserting pins P in the second pin hole 513b and a third pin hole 533c, so it is possible to prevent separation thereof.

Referring to FIG. 12, the ball receiving hole 513c is formed at a side of the bottom of the connecting portion 513, in detail, it is formed at a predetermined depth at a side of the top of the slide groove 513a to receive a portion of a ball B of a ball plunger to be described below to guide the cutting guide 3 and the adaptor 5 when they are locked and unlocked. To this end, the ball receiving hole 513c may include a first ball receiving hole 513c-1 and a second ball receiving hole 513c-2.

The first ball receiving hole 513c-1 is formed upward at a predetermined depth at a side of the top of the slide groove 513a and receives the ball B of the ball plunger to be described below to guide the cutting guide 3 and the guide adaptor 5 when they are locked. For example, it is possible to guide the pins P in the first pin holes 511a into the pin insertion holes 33. As described above, when the ball B inserted in a ball hole 533b to be described below is inserted into the first ball receiving hole 513c-1 by sliding the handle 51 to the aligner 3 after the first pin holes 511a and the pin insertion holes 33 are aligned, pins P are inserted into the pin insertion holes 33, so the guide adaptor 5 and the cutting guide are locked. Further, when the handle 51 and the aligning coupler 53 are coupled, the center point c1 of the first ball receiving hole 513c-1 is positioned on the axis 'a' of the third pin hole 533c to be described below so that the handle 51 can be accurately coupled to and decoupled from the cutting guide 3 by accurately sliding forward and backward the handle 51 coupled to the aligning coupler 53.

Referring to FIGS. 12 and 14, the second ball receiving hole 513c-2 is formed upward at a predetermined distance from the first ball receiving hole 513c-1 on the top of the slide groove 513a to guide the cutting guide 3 and the guide adaptor 5 when they are unlocked, by receiving the ball B of the ball plunger to be described below. For example, it is possible to guide the pins P in the pin insertion holes 33 when the pins are pulled out. Accordingly, when the handle 51 is slid in the opposite direction of the cutting guide 3 and the ball B is inserted into the second ball receiving hole 513c-2, the pins P are pulled out of the pin insertion holes 33, so the cutting guide 3 and the guide adaptor 5 can be unlocked. Further, when the handle 51 and the aligning coupler 53 are coupled, the center points c1 and c2 of the first ball receiving hole 513c-1 and the second ball receiving hole 513c-2 are positioned on the axis 'a' of the third pin hole 533c to be described below (see FIG. 16). Accordingly, the handle 51 is accurately guided when it is slid forward and backward to be coupled and decoupled, so it is possible to easily couple and decouple the handle 3 coupled to the aligning coupler 53 to and from the cutting guide 3.

Referring to FIGS. 13 and 14, the aligning coupler 53 is provided to couple the aligning member 11 and the cutting guide 3 such that they can slide, and to this end, it may have the member holders 531, an insertion rod 533, and the cross-shaped projections 535.

The member holders 531 are formed in pairs to face each other and form a groove having a predetermined shape on the inner sides. For example, a cross-shaped groove corresponding to the aligning member 11 is formed on the inner sides of the member holders 531 to receive the aligning member 11 that also has a corresponding shape so that the aligner 1 and the guide adaptor 5 can be coupled by sliding. Further, when the handle 51 is coupled to the aligning coupler 53 by sliding, the grips 511 press the member holders 531 positioned inside the grips, so it is possible to restrict slide of the member holders 531 with respect to the aligning member 11. Accordingly, the aligning member 11 and the adaptor 5 can be firmly coupled.

The insertion rod 533 is integrally formed with the member holders 531 and has a first side coupled to the handle 51 by sliding and a second side slid in the adaptor groove 31. To this end, the insertion rod 533 may have sliding flanges 533a, the ball hole 533b, the third pin hole 533c, a magnet hole 533d, chamfered edges 533e, and rounded corners 533f.

Referring to FIGS. 10, 13, and 14, the sliding flanges 533a is formed in a T-shape and protrude downward a predetermined length from the top of both sides of the insertion rod 533 so that the insertion rod 533 can be slid into the slide groove 513a.

The ball hole 533b is formed at a predetermined depth at a side on the top of the insertion rod 533 to receive the ball plunger therein. For example, as described above, the ball B at the end of the ball plunger inserted in the ball hole 533b is selectively inserted into the first ball receiving hole 513c-1 or the second ball receiving hole 513c-2, so it is possible to guide the cutting guide 3 and the adaptor 5 when they are locked and unlocked.

The third pin hole 533c is formed at a predetermined depth at the other side on the top of the insertion rod 533 to receive a pin P therein. The pin P inserted through the second pin hole 513b is received in the third pin hole, thereby preventing the handle 51 and the aligning coupler 53 from sliding forward and backward and separating. The third pin hole 533c may be formed in an oblong shape and enables the handle 51 coupled to the aligning coupler 53 by sliding to slide a predetermined distance forward and backward, whereby the cutting guide 3 and the adaptor 5 can be locked and unlocked.

Referring to FIGS. 13A and 13B, the magnet hole 533d is formed at a side on the proximal side of the insertion rod 533 to receive a magnet M therein. The type of the magnet is not limited, but, for example, it may be a neodymium magnet M, so the cutting guide 3 and the guide adaptor 5 can be firmly coupled by the attraction of the neodymium magnet M.

Referring to FIG. 14, the chamfered edges 533e, which are formed at a predetermined angle on both edges of the distal side of the insertion rod 533, reduce interference between edges when the aligning coupler 53 is inserted into the adaptor groove 31, so they can be easily coupled.

The rounded corners 533f, which are formed by rounding the bottom corners of the edges of the distal side of the insertion rod 533, can reduce interference between corners when the aligning coupler 53 is inserted into the adaptor groove 31. For example, even if the adaptor 5 is inclined, it can be easily inserted into the adaptor groove 31 of the tibial cutting guide 3 by the rounded corners 533f.

The cross-shaped projections 535, which have a hexahedral shape protruding with predetermined width and height from the aligning coupler 53, in detail, from a side on both sides of the insertion rod 533, are inserted in a second groove 317 of the adaptor groove 31, so it is possible to prevent the adaptor 5 from separating forward and backward from the tibial cutting guide 3. Accordingly, forward and backward separation of the cutting guide 3 and the guide adaptor 5 can be prevented by the cross-shaped projections 535 and their vertical separation can be prevented by inserting pins P into the first pin holes 511a.

Figure 15A:
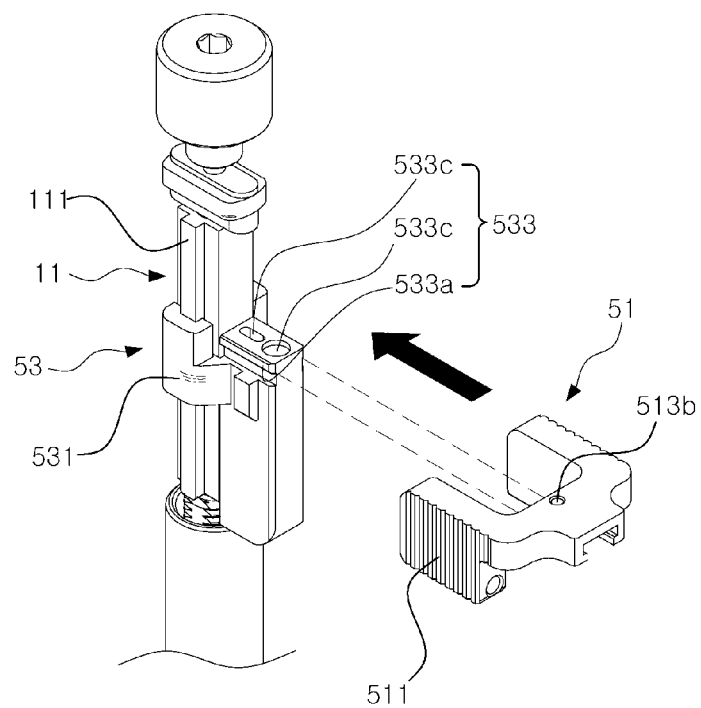
FIGS. 15A and 15B are a reference view of illustrating a process of combining the aligning member, the handle, and the aligning coupler.
Figure 15B:
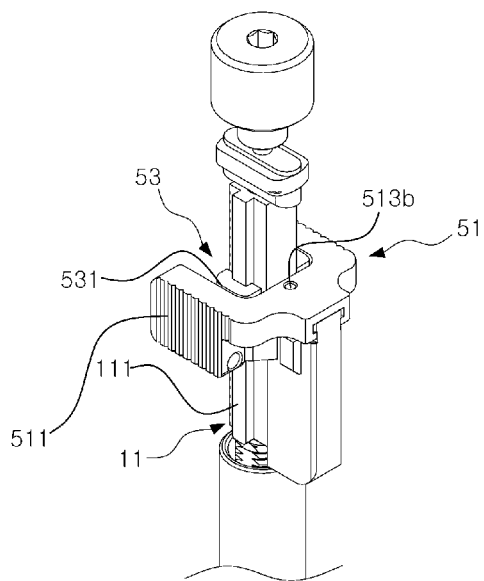
Figure 16:
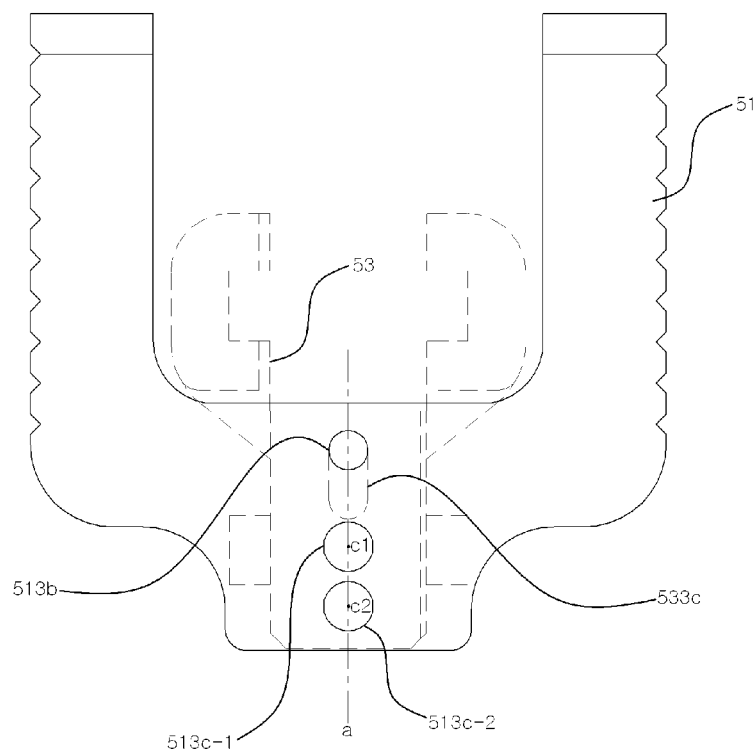
FIG. 16 is a reference view of illustrating the case when the center points of first and second ball receiving hole are positioned on the axis of a third pin slit.
Figure 17A:
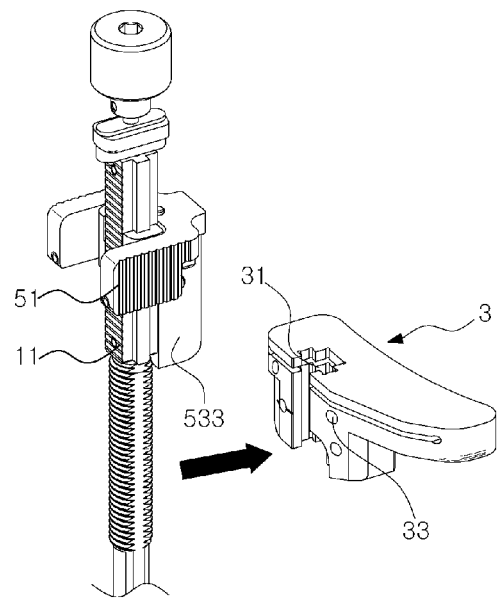
FIGS. 17A to 17C are reference views illustrating a process of combining (attaching) the aligning member and the tibial cutting guide through the guide adaptor.
Figure 17B:
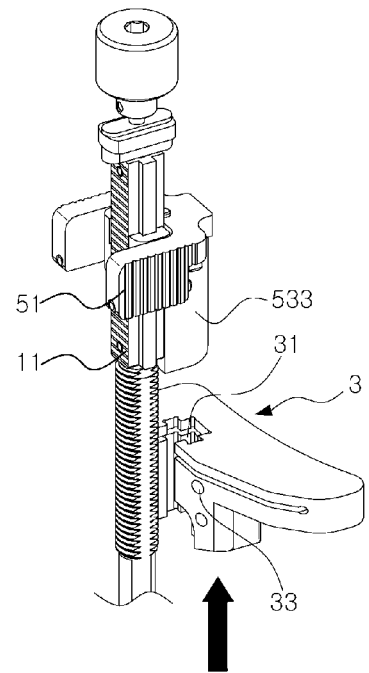
Figure 17C:
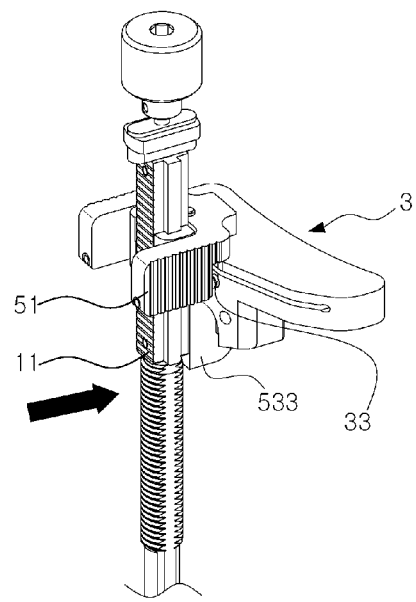
Figure 18A:
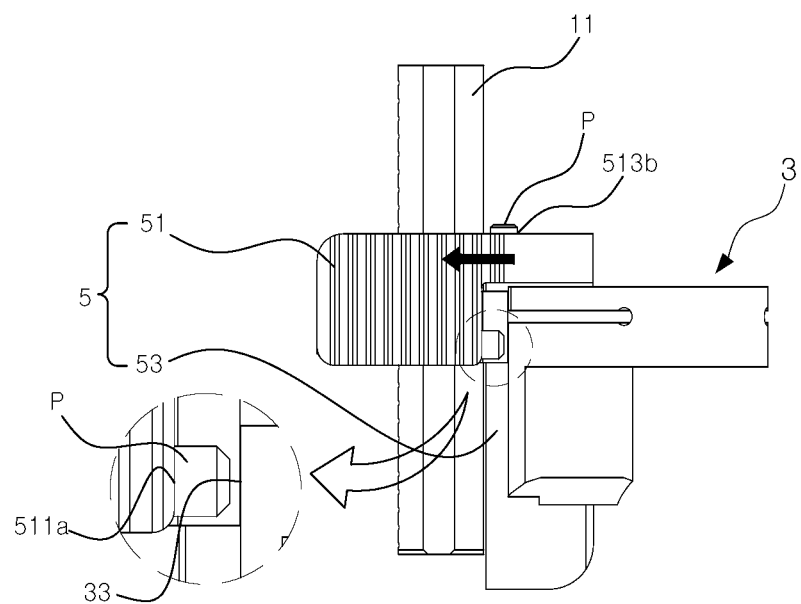
FIGS. 18A and 18B are reference views of detailedly illustrating a process of combining the cutting guide with the guide adaptor.
Figure 18B:
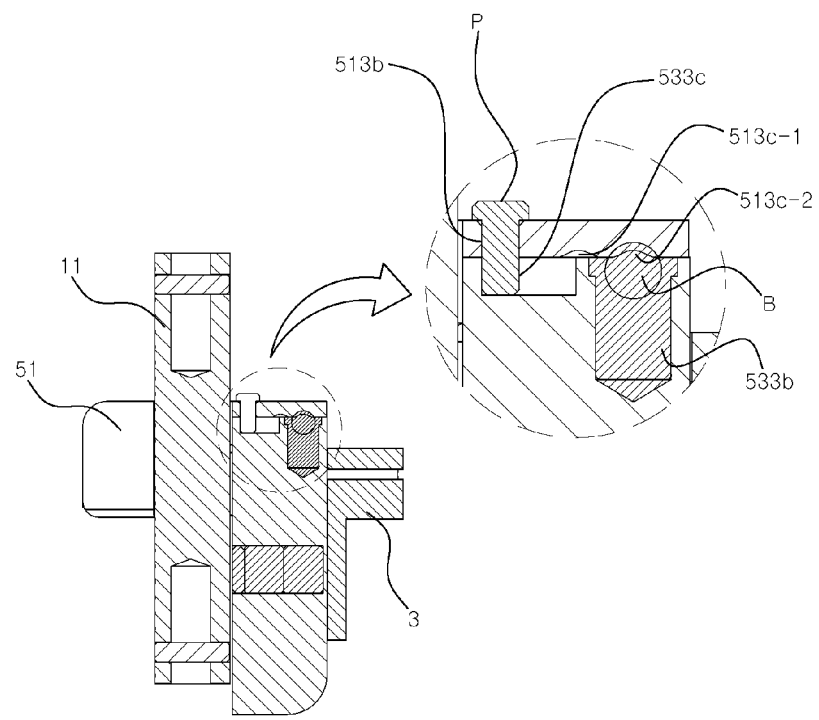
Figure 19A:
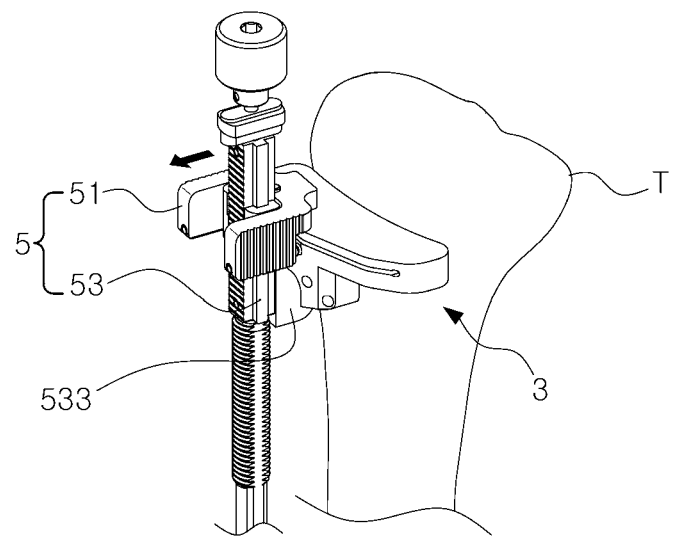
FIGS. 19A and 19B are reference views of illustrating a process of separating (detaching) the aligning member and the guide adaptor from the tibial cutting guide.
Figure 19B:
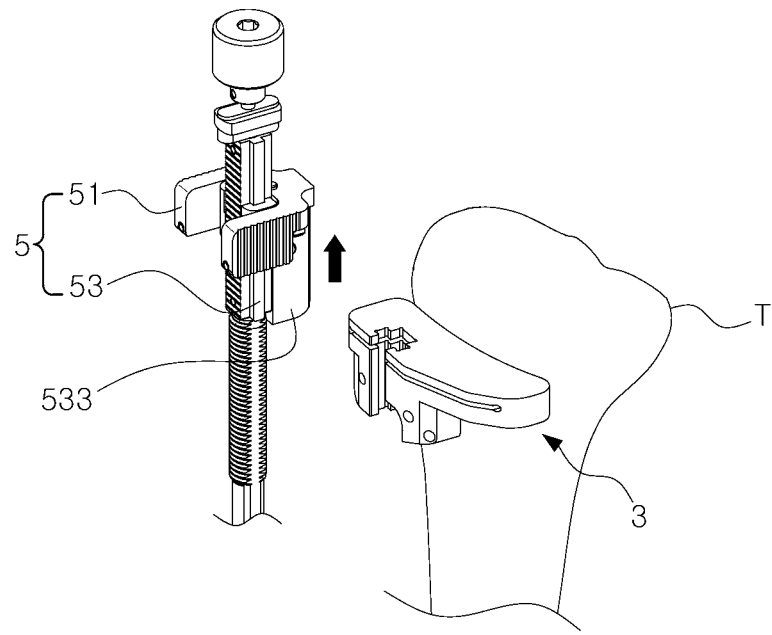
Figure 20A:
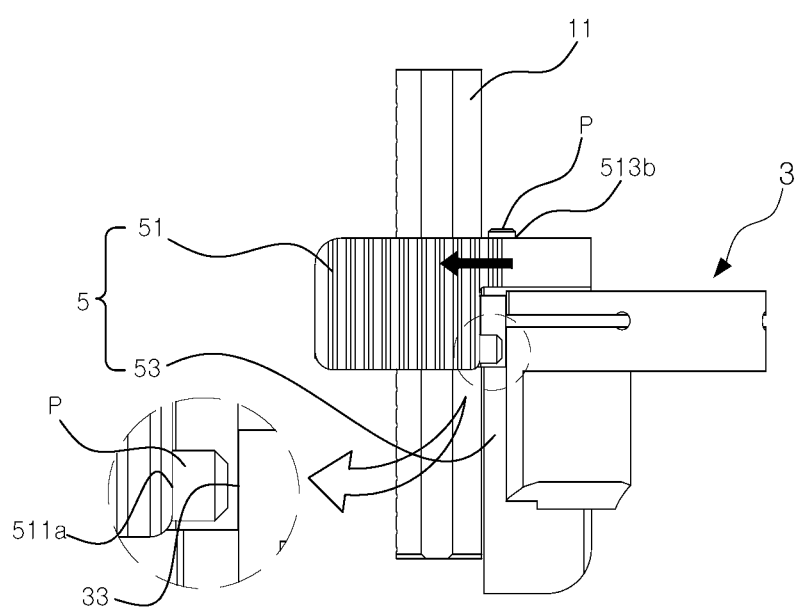
FIGS. 20A to 20B are reference views of detailedly illustrating a process of separating (detaching) the aligning member and the guide adaptor from the tibial cutting guide.
Figure 20B:
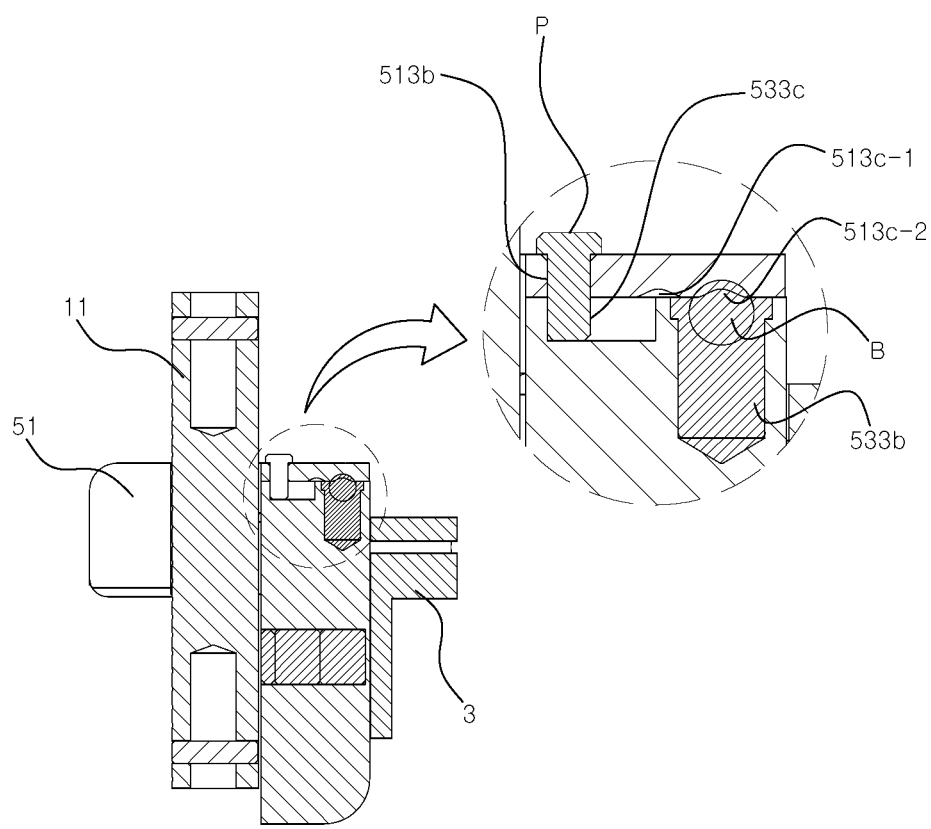

FIGS. 15A and 15B are a reference view for illustrating a process of combining the aligning member, the handle, and the aligning coupler, FIG. 16 is a reference view for illustrating the case when the center points of first and second ball receiving holes are positioned on the axis of a third pin slit, FIGS. 17A to 18B are reference views for illustrating a process of combining (attaching) the aligning member and the tibial cutting guide through the guide adaptor, and FIGS. 19A to 20B are reference views for illustrating a process of separating (detaching) the aligning member and the guide adaptor from the tibial cutting guide.

The method of combining the aligner 1 and the guide adaptor 5 through the coupler assembly for a tibial cutting guide is described with reference to FIGS. 15A and 15B. A side of the aligning member 11 is inserted into the groove between the member holders 531 and the aligning coupler 53 is slid, thereby the aligner and the guide adaptor are combined. Thereafter, the handle 51 and the aligning coupler 53 are combined by sliding through the sliding flanges 533a and the grips 511 press the member holders 531, whereby the aligning coupler 53 is fixed to a side of the aligning member 11. Thereafter, pins are inserted into the second pin hole 513b and the third pin hole 533c, thereby preventing the handle 51 from sliding over a predetermined level with respect to the aligning coupler 53. As described above, when the handle 51 and the aligning coupler 53 are coupled, the center points c1 and c2 of the first ball receiving hole 513c-1 and the second ball receiving hole 513c-2 are positioned on the axis 'a' of the third pin hole 533c to be described below (see FIG. 16).

Thereafter, the method of combining the tibial cutting guide 3 and the guide adaptor 5 through the coupler assembly for a tibial cutting guide is described with reference to FIGS. 17A to 18B. First, the aligning member 11 combined with the adaptor 5 is located close to the cutting guide 3. When they are coupled, the tibial cutting guide 3 aligns the bottom of the insertion rod 533 of the adaptor 5 with the adaptor groove 31 (see FIGS. 17B and 17C) and then the first pin holes 511a and the pin insertion holes 33 are aligned by sliding up the cutting guide 3. Thereafter, when the handle 51 is slid to the cutting guide 3, the pins P are inserted into the pin insertion holes 33, whereby the cutting guide 3 and the adaptor 5 are locked (see FIG. 18A). In this process, the ball B is received in the first ball receiving hole 513c-1, the locking can be guided (see FIG. 18B).

For separation, when the handle 51 is slid in the opposite direction without specific operation after the tibial cutting guide 3 is coupled to the proximal end of the tibia T, the pins P are pulled out, so the cutting guide 3 and the adaptor 5 are unlocked. In this process, the ball B is received in the second ball receiving hole 513c-2, so the locking can be guided (see FIG. 19A, FIG. 20A, and FIG. 20B). Thereafter, the insertion rod 533 is slid up out of the adaptor groove 31 by moving up the adaptor 5, whereby the aligner 1 and the cutting guide 3 can be separated (see FIG. 19B). Therefore, as described above, the guide adaptor 5 can be easily coupled and decoupled to and from the tibial cutting guide 3, so it is possible to minimize bleeding of a patient and aftereffects by reducing the surgical operation time.

Although various embodiments of the present invention by the applicant(s) were described above, the embodiments are just examples for achieving the spirit of the present invention and any modifications and changes should be construed as being included in the scope of the present invention as long as they can achieve the spirit of the present invention.

The invention claimed is:

1. A coupler assembly for a tibial cutting guide, the coupler assembly comprising a guide adaptor for holding the tibial cutting guide on an aligning member,
the guide adaptor including an aligning coupler slidably coupled to the aligning member and the cutting guide, and a handle slidably coupled to the aligning coupler;
the handle including a pair of grips formed in pairs facing each other to form a predetermined space therebetween, the handle sliding on the aligning coupler to be coupled to and decoupled from the cutting guide;
the grips each including a first pin hole formed at a side of each distal side at a predetermined depth to receive a pin;
when the handle is slid to the cutting guide with the first pin holes and pin insertion holes of the cutting guide aligned, the pins in the first pin holes are inserted into the pin insertion holes, so the handle and the cutting guide are locked; and
when the handle is slid in an opposite direction, the pins are pulled out of the pin insertion holes, so the handle and the cutting guide are unlocked.

2. The coupler assembly of claim 1, wherein the handle includes a slide groove that is formed with a predetermined length in a t-shape, the handle is detachably coupled to the aligning coupler by sliding the slide groove of the handle onto sliding flanges of the aligning coupler, the aligning coupler further including an insertion rod structured to slide into an adapter groove of the cutting guide such that the handle, the aligning coupler, and the cutting guide are detachably coupled to one another.

3. The coupler assembly of claim 2, wherein a direction in which the handle is slid with respect to the aligning coupler is substantially perpendicular to a direction in which the aligning coupler is slid onto the aligning member.

4. The coupler assembly of claim 3, wherein when the slide groove of the handle is slid onto the sliding flanges of the aligning coupler and when the insertion rod of the aligning coupler is slid into the adapter groove of the cutting guide, the handle is coupled to the cutting guide, so the cutting guide and the adaptor are locked.

5. The coupler assembly of claim 2, wherein:
a connecting portion of the handle includes the slide groove and is integrally formed with the grips;
the aligning coupler includes a pair of member holders facing each other and having comprises a groove of a predetermined shape on an inner side;
the insertion rod of the aligning coupler is integrally formed with the member holders; and
the sliding flanges of the aligning coupler are structured to protrude downward a predetermined length from tops of both sides so that the handle and the aligning coupler are coupled by sliding the sliding flanges through the slide groove of the handle.

6. The coupler assembly of claim 5, wherein when the handle and the aligning coupler are coupled by sliding the sliding flanges of the aligning coupler into the slide groove of the handle, the grips press the member holders positioned inside the grips, so sliding of the member holders with respect to the aligning member is restricted, whereby the aligning member and the guide adaptor can be firmly coupled.

7. The coupler assembly of claim 5, wherein the connecting portion further has a second pin hole formed vertically through a side to receive a pin,
the insertion rod further has a third pin hole formed at a predetermined depth at a side on a top to receive a pin, and
the handle is prevented from sliding from the aligning coupler by a pin inserted in the second pin hole and the third pin hole.

8. The coupler assembly of claim 7, wherein the third pin hole is formed in an oblong shape and enables the handle coupled to the aligning coupler by sliding to slide a predetermined distance forward and backward so that the cutting guide and the adaptor can be coupled and decoupled.

9. The coupler assembly of claim 8, wherein the insertion rod further has a ball receiving hole formed at a predetermined depth at another side on the top to receive a ball plunger therein, and the connecting portion further has a ball hole formed at a predetermined depth on a top of the slide groove and receives a ball of the ball plunger to guide the adaptor when the adaptor is locked and unlocked.

10. The coupler assembly of claim 9, wherein the ball receiving hole includes a first ball receiving hole formed at a predetermined depth at a side on the top of the slide groove and receives the ball in locking and a second ball receiving hole formed at a predetermined depth at a predetermined distance from the first ball hole and receives the ball in unlocking.

11. The coupler assembly of claim 10, wherein when the handle and the aligning coupler are coupled by sliding, center points of the first ball receiving hole and the second ball receiving hole are positioned on an axis of the third pin hole so that the adaptor and the cutting guide can be coupled and decoupled by accurately sliding the handle coupled to the aligning coupler.

12. The coupler assembly of claim 11, wherein the insertion rod further has a magnet hole formed at a side of a proximal side to receive a magnet therein, so the cutting guide and the guide adaptor can be firmly coupled by attraction of the magnet.

13. The coupler assembly of claim 12, wherein the magnet disposed in the magnet hole is a neodymium magnet.

14. The coupler assembly of claim 12, wherein the insertion rod further has chamfered edges to minimize interference between edges for easy coupling when the aligning coupler is inserted into the adaptor groove.

15. The coupler assembly of claim 12, wherein the insertion rod further has rounded corners formed by rounding bottoms of both edges of both sides of a distal side of the insertion rod to minimize interference between the edges for easy coupling when the insertion rod of the aligning coupler is inserted into the adaptor groove of the cutting guide.

* * * * *